Figure 1:
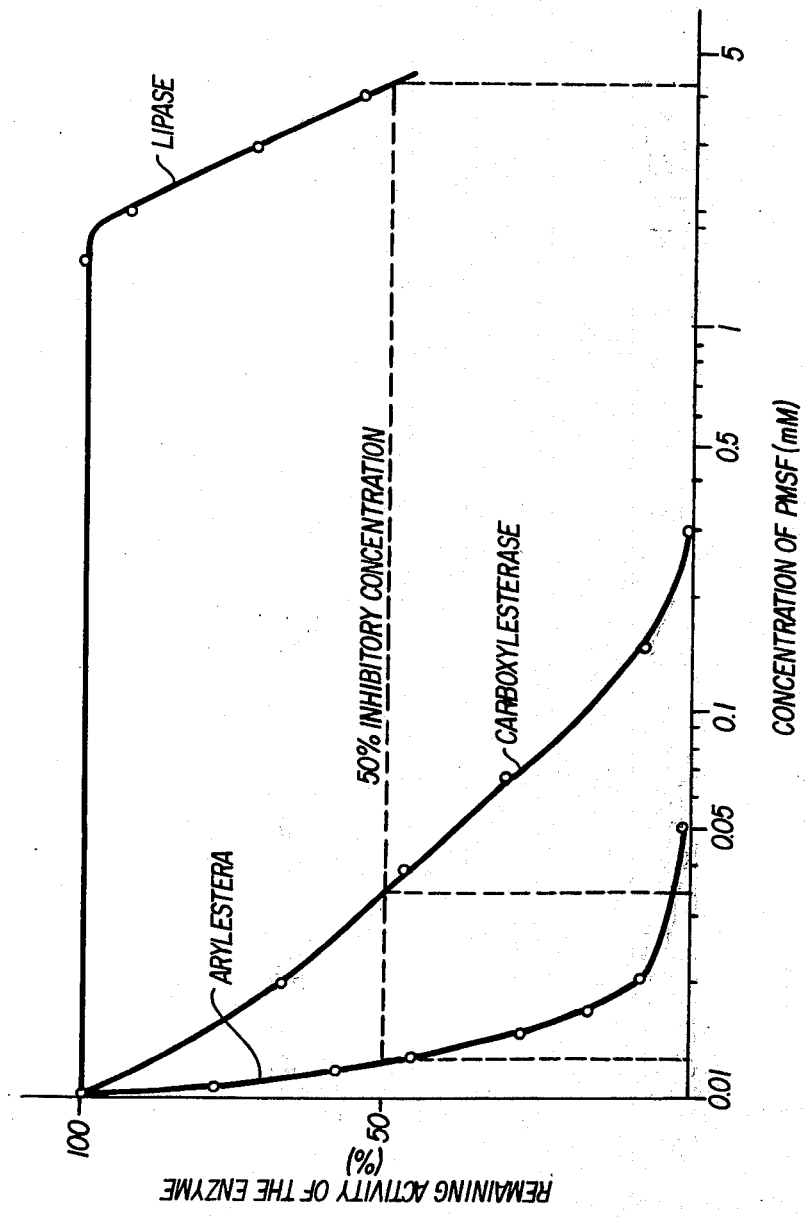

United States Patent [19]

Kurooka et al.

[11] 3,986,930
[45] Oct. 19, 1976

[54] LIPASE ACTIVITY DETERMINING METHOD AND REAGENT

[75] Inventors: Shigeru Kurooka, Fujiidera; Masahisa Hashimoto, Toyonaka; Masatsugu Tomita, Takatsuki; Akio Maki, Kyoto, all of Japan

[73] Assignee: Dainippon Pharmaceutical Co., Ltd., Osaka, Japan

[22] Filed: May 22, 1975

[21] Appl. No.: 579,910

[30] Foreign Application Priority Data
May 28, 1974 Japan................................. 49-60629
June 13, 1974 Japan................................. 49-67709
Sept. 13, 1974 Japan............................... 49-106295

[52] U.S. Cl............................. 195/103.5 R; 195/99
[51] Int. Cl.$^2$........................ C12K 1/04; C12K 1/10
[58] Field of Search..................... 195/103.5 R, 99; 424/335; 260/455 R

[56] References Cited
OTHER PUBLICATIONS

J. F. Whitaker "A Rapid and Specific Method for the Determination of Pancreatic Lipase in Serum and Urine" Clinica Chimica Acta, 44 (1973) 133–138.
F. P. Doyle et al., "Antituberculous Sulphur Compounds, Part II" J. Chem. Soc. 2660–2665 (1960).

*Primary Examiner*—A. Louis Monacell
*Assistant Examiner*—C. A. Fan
*Attorney, Agent, or Firm*—Stevens, Davis, Miller & Mosher

[57] ABSTRACT

A reagent for determining lipase activity, which comprises as the active ingredient one of the S-acyl compounds of the formula:

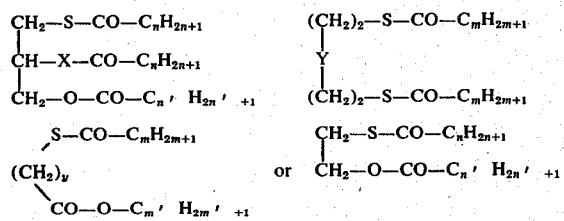

wherein $n$ is an integer of 2 to 4, inclusive; $n'$ is an integer of 2 to 4, inclusive or of 9 to 13, inclusive; $m$ is an integer of 3, 7 or 11; $m'$ is an integer of 4 or 12; $y$ is an integer of 1 or 2; X is sulfur atom or oxygen atom; Y is sulfur atom, oxygen atom or ethylene group; provided that when $y$ is 1, $m'$ is 4 and when $y$ is 2, $m'$ is 12, and a method for determining lipase activity by reacting the S-acyl compound with lipase in a buffer solution containing a chromogenic sulfhydryl reagent and then subjecting the resultant to a colorimetry.

41 Claims, 2 Drawing Figures

LIPASE ACTIVITY DETERMINING METHOD AND REAGENT

The present invention relates to a reagent for determining lipase activity comprising as an active ingredient an S-acyl compound and a method for determining lipase activity. More particularly, it relates to a reagent for determining lipase activity comprising as the active ingredient one of the following S-acyl compounds:

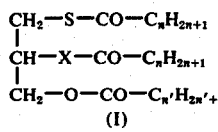
(I)

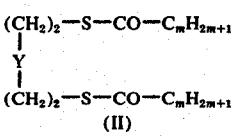
(II)

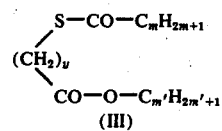
(III)

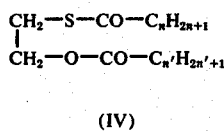
(IV)

wherein $n$ is an integer of 2 to 4, inclusive; $n'$ is an integer of 2 to 4, inclusive or of 9 to 13, inclusive; $m$ is an integer of 3, 7 or 11; $m'$ is an integer of 4 or 12; $y$ is an integer of 1 or 2; X is sulfur atom or oxygen atom; Y is sulfur atom, oxygen atom or ethylene group; provided that when $y$ is 1, $m'$ is 4 and when $y$ is 2, $m'$ is 12.

The reagent for determining lipase activity of the present invention can be widely applied to, for instance, the determination of lipase activity in body fluids and extracts of various tissues in human and other animals or in extracts of bacteria, the approval of standard lipase product, or the like, and it is particularly useful for determining lipase activity in human serum. It is well known that serum lipase activity is elevated in patients with pancreatic diseases, and therefore, the present reagent is very useful clinically as a diagnostic agent. According to the present method, the development of color intensity in proportion to serum lipase level proceeds from the start of the reaction, and therefore, the kit prepared based on this method is of great use for the rapid diagnosis of acute pancreatitis in a state of emergency.

There have, hitherto, been known various methods for determining lipase activity as follows:

1. A turbidimetric method comprising reacting lipase with olive oil and then measuring optically the decrease in the turbidity (cf. P. A. Verduin et al, Clin. Chim., Acta. Vol. 46, pages 11–19, 1973)

2. An alkalimetric method comprising reacting lipase with olive oil and then subjecting the released fatty acid to an alkalimetry (cf. J. H. Roe et al, Analytical Biochem., Vol. 6, pages 451–460, 1963)

3. A colorimetric method comprising reacting lipase with olive oil and then subjecting the resulting free fatty acid or glycerin to any colorimetry, for instance, by adding a copper salt to the free fatty acid and extracting the resultant with n-hexane, adding sodium diethylthiocarbamate to the extract and then subjecting the mixture to a colorimetry (cf. R. Fried et al, Z. Klin. Chem. Biochem., Vol. 11, pages 189–192, 1973)

4. A colorimetric method comprising reacting lipase with a synthetic substrate and then subjecting the resulting hydrolyzed product to any colorimetry, for instance, reacting lipase with α-naphthyl palmitate, followed by coupling the released α-naphthol with a diazonium salt and then subjecting the colored resultant to a colorimetry (cf. J. F. Whitaker et al., Clinica Chimica Acta, Vol. 44, pages 133–138, 1973).

However, according to these known methods, the sensitivity is not so high and a comparatively large amount of sample to be tested is required. Moreover, the known methods have some other defects such as difficulty in the assay procedures, poor stability of the substrate, or the like.

The site of the action of lipase is the interface between the oil and the aqueous phases. Besides, when olive oil is used as the substrate, it is necessary to enhance the reaction rate of the lipase by increasing the substrate concentration at the interfaces between aqueous and oil layers. For this purpose, the olive oil is prepared in the form of emulsion by adding thereto an emulsifier (e.g. gum arabic or bile salts) or by stirring vigorously. However, the olive oil emulsion thus prepared is not stable and can not be kept for more than several weeks even when maintained at a temperature near 0° C.

Under the circumstances, the present inventors have intensively studied to find an improved method for determining lipase activity and have found that specific S-acyl compounds are useful as substrates for the colorimetric determination of lipase activity.

An object of the present invention is to provide an improved reagent for determining lipase activity.

Another object of the invention is to provide an improved method for the colorimetric determination of lipase activity.

A further object of the invention is to provide a convenient method for determining lipase activity in human serum.

A more further object of the invention is to provide a diagnostic agent for pancreatic diseases.

A still further object of the invention is to provide a diagnostic kit for pancreatic diseases.

These and other objects of the invention will be apparent from the description hereinafter.

According to the present invention, the lipase activity can be easily determined by using as the substrate one of S-acyl compounds having the formulae (I), (II), (III) and (IV).

Suitable examples of the S-acyl compounds (I), (II), (III) or (IV) are shown in Table 1.

Table 1

| | X | Y | n | n' | m | m' | y | Remark |
|---|---|---|---|---|---|---|---|---|
| $CH_2-S-CO-C_nH_{2n+1}$ $\mid$ $CH-X-CO-C_nH_{2n+1}$ $\mid$ $CH_2-O-CO-C_{n'}H_{2n'+1}$ | S | | 3 | 3 | | | | *1 |
| | O | | 3 | 3 | | | | *2 |
| | S | | 3 | 11 | | | | |

Table 1-continued

| X | Y | n | n' | m | m' | y | Remark |
|---|---|---|----|---|----|---|--------|
| (CH₂)₂—S—CO—C_mH_{2m+1} <br> \| <br> Y <br> \| <br> (CH₂)₂—S—CO—C_mH_{2m+1} | —(CH₂)₂— | | | 3 | | | |
| (same) | S | | | 3 | | | |
| (CH₂)_y branched: S—CO—C_mH_{2m+1} and CO—O—C_{m'}H_{2m'+1} | | | | 3 <br> 11 | 12 <br> 12 | 2 <br> 2 | |
| CH₂—S—CO—C_nH_{2n+1} <br> \| <br> CH₂—O—CO—C_{n'}H_{2n'+1} | | 3 <br> 3 <br> 2 | 11 <br> 3 <br> 11 | | | | *3 |

[Note]:
*1 This compound is, hereinafter, referred to as "BALB".
*2 This compound is, hereinafter, referred to as "MPB".
*3 This compound is, hereinafter, referred to as "BLME".

Among these compounds, the most suitable compounds are BALB and MPB.

The determination of lipase activity by the present invention is carried out based on the following principle. That is, a solution of the substrate [an S-acyl compound of the formula (I), (II), (III) or (IV)] in an alcohol is added to the reaction buffer solution containing the sample with lipase and a chromogenic sulfhydryl reagent which reacts with a SH-group-containing compound [hereinafter, referred to as "SH-compound"] released from the substrate by lipase. The amount of the released SH-compound or the intensity of the colored reaction mixture is proportional to the lipase activity in the sample, and therefore, the lipase activity can be determined by subjecting the resulting colored reaction mixture to colorimetric readings. As a sulfhydryl reagent, 5,5'-dithiobis(2-nitrobenzoic acid) [hereinafter, referred to as "DTNB"] is used. In case of the measurement of lipase activity by using the S-acyl compound (I) (X is O) and DTNB, it is assumed that the reaction will proceed as shown in the following scheme:

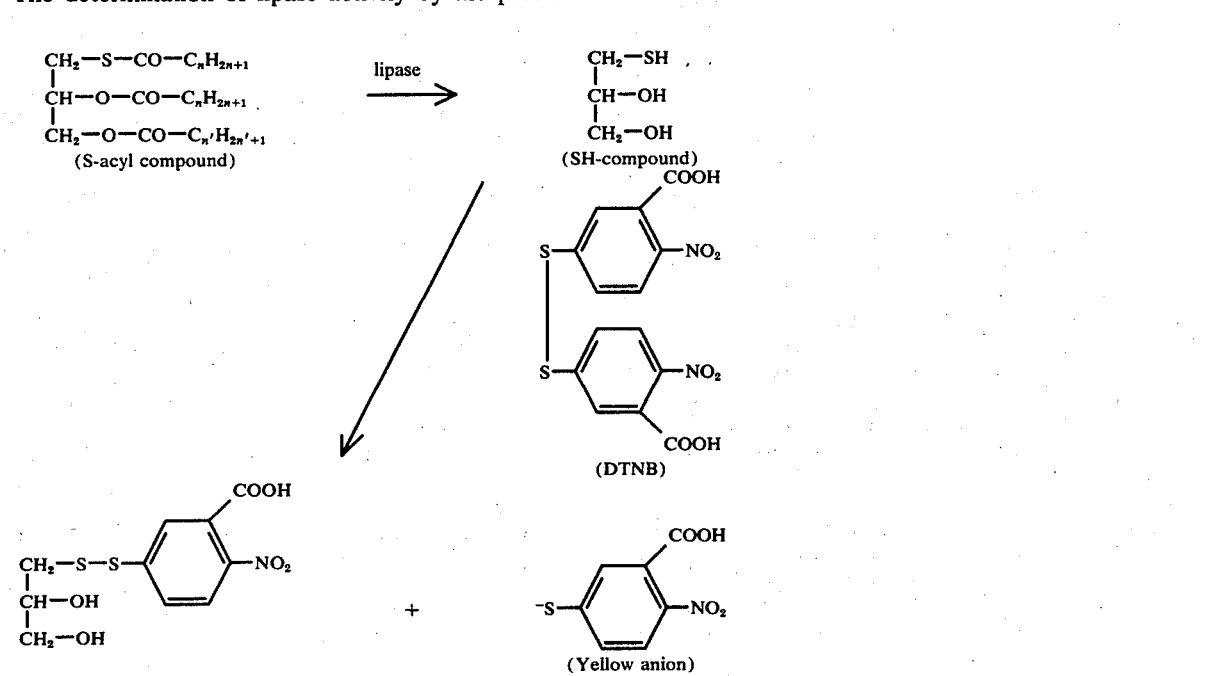

There has never been known any method for determining lipase activity by using the synthetic substrate of the formula (I), (II), (III) or (IV) on the basis of such principle as above.

According to the present method, the measurement of lipase activity can be easily carried out by using so small amount of sample as 1/10 to 1/100 of that in the known methods described hereinbefore and within a shorter time. Moreover, the substrate becomes micellar merely by mixing and shaking with a buffer solution without addition of an emulsifier or vigorous stirring, and further, the solution of the substrate in an alcohol is stable at room temperature for more than 6 months.

It has been also reported that a certain synthetic glyceride such as tributyrin (i.e. glyceryl tributyrate), which has a similar structure to that of the present S-acyl compounds, is used for determining lipase activity, but this method is carried out by a different principle of that of the present invention and the reagent has a low sensitivity and lacks in substrate specificity, and therefore, this method is not practically used.

According to the present method, the lipase activity is determined by hydrolyzing the substrate with lipase and then measuring the amount of the released SH-compound. If the lipase-containing sample to be tested contains other enzymes which hydrolyze the substrate, the determination of lipase activity can not be done. Generally, the enzymes being capable of hydrolyzing a carboxylic acid ester are classified as follows:

1. Carboxylesterase (Enzyme Commission No. [3.1.1.1])
2. Arylesterase (Enzyme Commission No. [3.1.1.2])
3. Lipase (Enzyme Commission No. [3.1.1.3])

Thus, if the sample to be tested contains these carboxylesterase and/or arylesterase as well as lipase, the substrate is also hydrolyzed by these other enzymes to produce an SH-compound. Accordingly, when the test sample is possible to contain these carboxylesterase and/or arylesterase in addition to lipase, it is necessary to add to the test sample an enzyme inhibitor which can specifically inactivate both carboxylesterase and arylesterase. Suitable examples of the enzyme inhibitor are phenylmethylsulfonyl fluoride ($C_6H_5CH_2SO_2F$; hereinafter, referred to as "PMSF") and diisopropylfluorophosphate

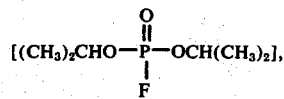

and the most suitable one is PMSF.

By the way, when the test sample does not contain such carboxylesterase and/or arylesterase, as in case of the approval of standard lipase product, it is needless to add such an enzyme inhibitor.

According to the present invention, the determination of lipase activity may be usually carried out in the following manner.

To a buffer solution are added a solution of a chromogenic sulfhydryl reagent (e.g. DTNB) and a lipase-containing solution (test sample) and optionally a solution of enzyme inhibitor (e.g. PMSF) in an alcohol, by which the coexistent carboxylesterase and/or arylesterase are specifically inactivated, and thereto is added a solution of a substrate [an S-acyl compound of the formula (I), (II), (III) or (IV)]. The mixture is incubated for an appropriate time, and thereafter, the reaction is stopped by addition of acetone which clears the turbid substrate. The resulting mixture, which contains the produced yellow anion, is subjected to a colorimetry, that is, the optical density of the mixture is measured at 400 - 420 m$\mu$, preferably at 412 m$\mu$.

The method of the present invention may be carried out under the following conditions.

1. Buffer: any buffer used in a conventional enzymatic reaction can be used. The most suitable one is Tris-HCl buffer.
2. pH value: at 7.5 - 10, preferably at 8.5 - 9.0
3. Temperature of incubation: 30° – 40° C
4. Incubation time: not more than 120 minutes 5. Concentration of the substrate: 1.3 - 2.6 mM (the apparent Michaelis constant of BALB and MPB for lipase: about $4 \times 10^{-4}$M)
6. Concentration of enzyme inhibitor (e.g. PMSF): generally 0.03 - 3 mM, preferably 0.1 - 1.5 mM, more preferably, 0.2 - 0.8 mM.

Each reagent used in the present determination of lipase activity is preserved in the form suitable to each reagent.

For instance, most of the substrates of the formulae (I), (II), (III) and (IV) are liquid at room temperature and may be preserved in the form of a solution in an alcohol (e.g. ethanol).

When an aqueous solution of the chromogenic sulfhydryl reagent (e.g. DTNB) is kept for a long time, it turns yellow, and therefore, the reagent is preferably preserved in the form of a powder and the aqueous solution thereof is prepared when it is used. The powder of DTNB may be mixed with an inert other powder (e.g. mannitol) for the purpose of making it easily weighed.

The buffer may be preserved in the form of a solution, but in view of the bacterial contamination and inconvenience of its transference, the reagent is preferably kept in the powder form, and dissolved in water when used.

The enzyme inhibitor (e.g. PMSF) is preferably preserved in the form of an alcoholic solution (e.g. ethanolic solution). PMSF in an alcohol solution is stable even if it is heated at 120° C for 30 minutes, but if the solution is mixed with the substrate (I), (II), (III) or (IV) in an alcohol, PMSF undergoes chemical reaction with the substrate to lose its action as an esterase-inhibitor, and therefore, both of the solutions must be preserved separately.

These reagents may be preferably kept as kits for lipase assays for many months at room temperature in appropriate package sizes suitable for determining 50 to 100 samples.

Amont the S-acyl compounds used in the present invention, the compound of the formula (I) wherein X is sulfur atom is known as an antituberculosis agent (J. Chem. Soc., 2660, 1960), but its utility for the determination of the lipase activity has never been known. The compounds of the formula (I) wherein X is oxygen atom and the compounds of the formula (II), (III) or (IV) are novel and can be prepared by acylating the corresponding thio-alcohol with an acid derivative, such as an acid, acid halide or acid anhydride in a similar manner as described in J. Chem. Soc., 2660, 1960.

The preparation of the reagent of the present invention, the method for determining the lipase activity thereby and the preparation of the S-acyl compounds used therein are illustrated by the following Examples, but not limited thereto.

EXAMPLE 1

Preparation of the present reagent
a. 20 mM BALB/ethanol solution:
BALB (669 mg) is dissolved in ethanol to make a final volume of 100.0 ml.
a'. 20 mM MPB/ethanol solution:
MPB (636 mg) is dissolved in ethanol to make a final volume of 100.0 ml.
a''. 20 mM BLME/ethanol solution:

BLME (660 mg) is dissolved in ethanol (about 50 ml) and thereto is added ethanol to make a final volume of 100.0 ml.

b. 20 mM PMSF/ethanol solution:

PMSF (348 mg) is dissolved in ethanol to make a final volume of 100.0 ml.

c. 0.3 mM DTNB/0.1 M Tris-HCl (pH 8.5):

DTNB (12.0 mg) is completely dissolved in 1M Tris-HCl buffer (10.0 ml) and thereto is added water to make a final volume of 100.0 ml.

d. Acetone (guaranteed reagent)

EXAMPLE 2

Determination of lipase activity (substrate: BALB)

Reagent a. 20 mM BALB/ethanol solution
b. 20 mM PMSF/ethanol solution
c. 0.3 mM DTNB/0.1 M Tris-HCl (pH 8.5)
d. Acetone Method To test tubes I and II are added (c) (1 ml) and a test sample (10 – 1,500 BALB unit of lipase or about 10 μl of human serum), and further to the test tube I is added (b) (20 μl; the concentration of PMSF: about 0.4 mM) and the mixture is allowed to stand at room temperature for 5 minutes to inactivate the existing serum caboxylesterase and/or arylesterase.

To the test tube I is further added a substrate (a) (0.1 ml). The test tubes I and II are kept for 30 minutes at 38° C, and immediately to the test tube II is added the substrate (a) (0.1 ml) and to these test tubes I and II is added acetone (d) (2 ml) to stop the reaction. After mixed well, the tubes I and II were centrifuged (700 × g, for 10 minutes) to remove insoluble serum proteins and turbidity due to serum lipids and the substrate. The optical density of the supernatant of the tube I is measured at 412 nm in a cuvette of 1 cm light path ($OD_{412}^{1\ cm}$) against that of the tube II. The value of $[OD_{412}^{1\ cm} (I - II) \times 1,000]$ shows BALB unit of lipase.

Besides, test tube III is treated in the same manner as test tube I except that the enzyme inhibitor (b) is omitted. The value of $[OD_{412}^{1\ cm} (III - I) \times 1,000]$ shows the total activity of the arylesterase and carboxylesterase.

EXAMPLE 3

Determination of lipase activity (substrate: MPB)

Reagent a'. 20 mM MPB/ethanol solution
b. 20 mM PMSF/ethanol solution
c. 0.3 mM DTNB/0.1 M Tris-HCl (ph 8.5)
d. Acetone Method In the same manner as described in Example 2, the determination of lipase activity is carried out except that the substrate (a') is used instead of (a).

EXAMPLE 4

The lipase activity and the total activity of carboxylesterase and arylesterase in the serum sample obtained from normal subjects and patients with pancreatic and hepatic diseases are measured in the same manner as described in Example 2 (serum: 10 μl, substrate: BALB). The results are shown in Table 2.

Table 2

| Serum | Diseases | Lipase $OD_{412}^{1\ cm}(I-II) \times 10^3$ | Carboxylesterase + arylesterase $OD_{412}^{1\ cm}(III-I) \times X 10^3$ |
|---|---|---|---|
| A | Normal | 18 | 68 |
| B | " | 17 | 61 |
| C | " | 20 | 60 |
| D | " | 11 | 60 |
| E | " | 19 | 18 |
| F | " | 18 | 62 |
| G | " | 20 | 50 |
| H | Acute pancreatitis | 379 | 120 |
| I | Cancer of head of the pancreas | 290 | 45 |
| J | " | 186 | 63 |
| K | " | 125 | 40 |
| L | Acute pancreatitis | 85 | 87 |
| M | " | 127 | 61 |
| N | " | 187 | 136 |
| O | Acute hepatitis | 30 | 469 |
| P | Hepatitis | 17 | 198 |
| Q | " | 0 | 72 |
| R | " | 6 | 106 |

As is made clear from the above results, in normal subjects and patients with acute hepatitis, the lipase activity in the serum is less than 30 BALB units, but in the patients with pancreatic diseases, the lipase activity in the serum is over 85 BALB units. Besides, the total activity of carboxylesterase and arylesterase $[OD_{412}^{1\ cm} (III - I) \times 1,000]$ is low in the normal subjects and the patients with pancreatic diseases, but that in the patients with acute hepatitis is abnormally high.

In cases of using MPB or BLME as the substrate, the similar results are obtained.

EXAMPLE 5

In the same manner as described in Example 2, the determination of lipase activity is carried out on the human serum (10 μl) containing lipase of 30,000 BALB unit/ml (substrate: BALB). When the determination is carried out 20 times, the averate ± standard deviation is 298.4 ± 9.7.

EXAMPLE 6

In the same manner as described in Example 3, the determination of lipase activity is carried out on the human serum (10 μl) containing lipase of 20,000 MPB unit/ml (substrate: MPG). When the determination is carried out 20 times, the average ± standard deviation is 200 ± 10.

EXAMPLE 7

By using BLME as the substrate, the determination of lipase activity on a human serum sample (20 μl) containing lipase (about 4,000 BLME unit/ml) is carried out twice per day for 10 days (totally 20 times). The results are shown in Table 3.

Table 3

| Day | BLME unit/20 μl serum First | Second | Average | Day | BLME unit/20 μl serum First | Second | Average |
|---|---|---|---|---|---|---|---|
| 1 | 83 | 70 | 76.5 | 6 | 75 | 80 | 77.5 |
| 2 | 77 | 76 | 76.5 | 7 | 78 | 85 | 81.5 |
| 3 | 77 | 80 | 78.5 | 8 | 73 | 78 | 75.5 |
| 4 | 77 | 72 | 74.5 | 9 | 77 | 78 | 77.5 |
| 5 | 80 | 68 | 74.0 | 10 | 77 | 75 | 76.0 |

Average: 76.8
Standard deviation: 4.0

Table 3-continued

Coefficient of variation: 5.2%

EXAMPLE 8

In the same manner as described in Example 2, lipase of 1,100 BALB unit, carboxylesterase of 450 BALB unit or arylesterase of 60 BALB unit is treated (substrate: BALB), wherein the concentration of PMSF is varied, and then the rate of hydrolysis of BALB (relative activity) is measured. The results are shown in FIG. 1.

The 50 % inhibitory concentration of PMSF is $4.2 \times 10^{-3}$ M for lipase, $3.5 \times 10^{-5}$ M for carboxylesterase and $1.2 \times 10^{-5}$ M for arylesterase. Thus, the 50 % inhibitory concentration for carboxylesterase or arylesterase is about 1/100 or 1/300 of that for lipase, respectively. Even if the amount of the lipase, carboxylesterase and arylesterase is increased or decreased several times, the results are almost the same.

Accordingly, unless the conditions as mentioned in Example 2 are largely changed, in case of the determination of lipase activity by using BALB as the substrate, the useful concentration of PMSF is 0.05 – 2 mM, preferably 0.3 – 1.5 mM, more preferably 0.4 – 1.0 mM.

EXAMPLE 9

Figure 2:
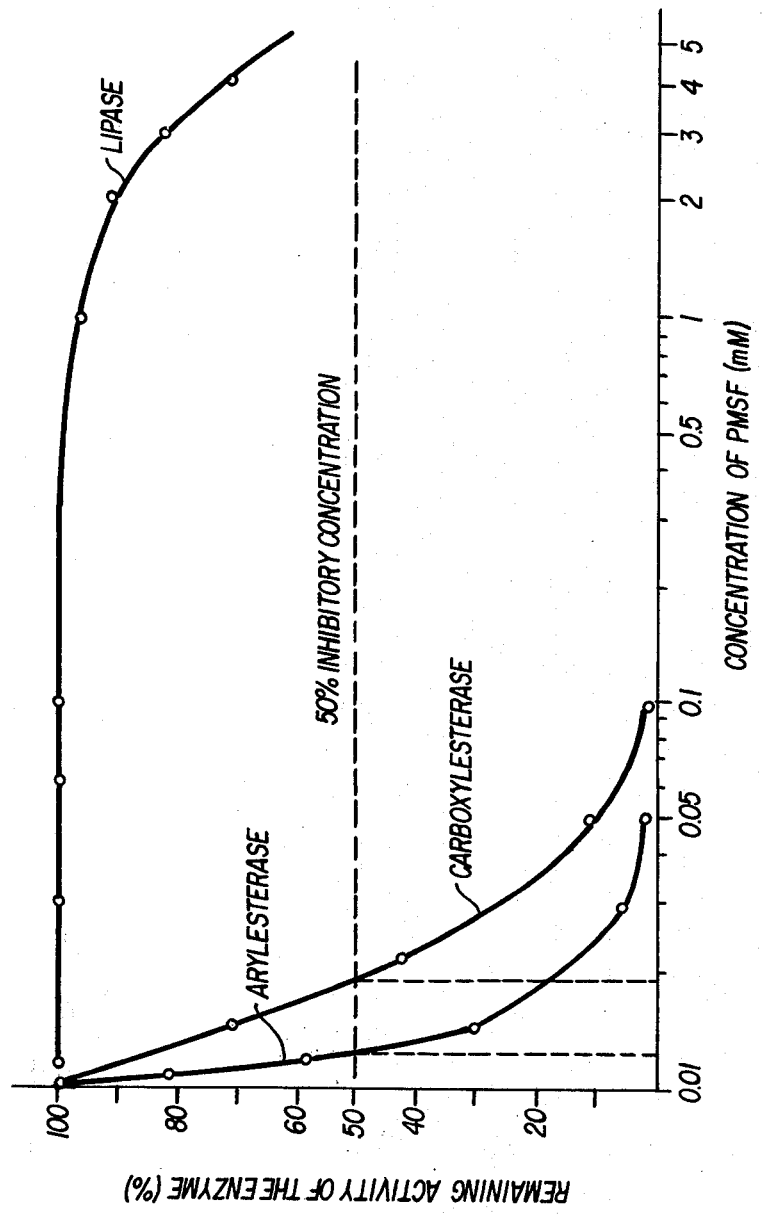

In the same manner as described in Example 3, lipase of 1,100 MPB unit, carboxylesterase of 140 MPB unit or arylesterase of 68 MPB unit is treated (substrate: MPB), wherein the concentration of PMSF is varied, and then the rate of hydrolysis of MPB (relative activity) is measured. The results are shown in FIG. 2.

The 50 % inhibitory concentration of PMSF is about $4 \times 10^{-3}$ M for lipase, about $2 \times 10^{-5}$ M for carboxylesterase and about $1 \times 10^{-5}$ M for arylesterase. Thus, the 50 % inhibitory concentration for carboxylesterase or arylesterase is about 1/200 or 1/400 of that for lipase, respectively. Even if the amount of the lipase, carboxylesterase and arylesterase is increased or decreased several times, the results are almost the same.

Accordingly, unless the conditions as mentioned in Example 3 are largely changed, in case of the determination of lipase activity by using MPB as the substrate, the useful concentration of PMSF is 0.05 – 1 mM, preferably 0.1 – 1.0 mM, more preferably 0.2 – 0.8 mM.

EXAMPLE 10

In the same manner as described in Example 9, the determination of lipase activity is carried out by using BLME as the substrate. Inhibition of the lipase activity in the presence of 0 – 2.0 mM of PMSF is negligible, whereas the carboxylesterase activity is inhibited about 90 % or more in the presence of 0.2 mM or more of PMSF.

EXAMPLE 11

Purified hog pancreatic lipase (type IV, a product of Sigma Chemical Co.) is dissolved in 1 % human serum albumin solution to give a solution (10 μg/ml). The lipase activity in 10 μl of this solution (corresponding to 0.1 μg of lipase) is determined in the same manner as described in Example 2 (substrate: BALB) in the absence of PMSF. The lipase activity measured is 800 BALB units.

One μmole of the released SH-group from the substrate gives 4.75 of $OD_{412}{}^{1\ cm}$ under the conditions described in Example 11, and therefore 1 mg of the purified hog pancreatic lipase is calculated to hydrolyze the S-acyl group of the BALB to give a free SH-group at the rate of 1,670 μmoles/30 minutes.

EXAMPLE 12

The same lipase solution (10 μl) as prepared in Example 11 is treated in the same manner as described in Example 2 by using various S-acyl compounds as the substrate in the absence of PMSF. The relative activity of the S-acyl compounds are measured. The results are shown in Table 4, wherein the relative activity of BLME for lipase is expressed as 100.

Table 4

| | X | Y | n | n' | m | m' | y | Relative activity (%) | Remark |
|---|---|---|---|---|---|---|---|---|---|
| $CH_2-S-CO-C_nH_{2n+1}$<br>\|<br>$CH-X-CO-C_nH_{2n+1}$<br>\|<br>$CH_2-O-CO-C_{n'}H_{2n'+1}$ | S<br>O<br>S<br>S<br>S<br>S<br>O<br>S | | 3<br>3<br>2<br>4<br>3<br>1<br>1<br>11 | 3<br>3<br>2<br>4<br>11<br>1<br>1<br>11 | | | | 500<br>250<br>305<br>135<br>420<br>10<br>5<br>1.5 | BALB<br>MPB<br><br><br>*<br>*<br>*<br>* |
| $(CH_2)_2-S-CO-C_mH_{2m+1}$<br>\|<br>Y<br>\|<br>$(CH_2)_2-S-CO-C_mH_{2m+1}$ | | $-(CH_2)_2-$<br>$-(CH_2)_2-$<br>S<br>O<br>O<br>$-(CH_2)_2-$ | | | 3<br>7<br>3<br>3<br>5<br>5 | | | 170<br>105<br>158<br>110<br>5<br>5 | <br><br><br><br>*<br>* |
| $S-CO-C_mH_{2m+1}$<br>\|<br>$(CH_2)_y$<br>\|<br>$CO-O-C_{m'}H_{2m'+1}$ | | | | | 3<br>11<br>3<br>7<br>3<br>11 | 12<br>12<br>4<br>4<br>12<br>4 | 2<br>2<br>1<br>1<br>1<br>2 | 163<br>160<br>125<br>130<br>15<br>7.5 | <br><br><br><br>*<br>* |

Table 4-continued

| | X | Y | n | n' | m | m' | y | Relative activity (%) | Remark |
|---|---|---|---|---|---|---|---|---|---|
| $\begin{array}{l}CH_2-S-CO-C_nH_{2n+1}\\|\\CH_2-O-CO-C_{n'}H_{2n'+1}\end{array}$ | | | 3 | 11 | | | | 100.0 | BLME |
| | | | 2 | 11 | | | | 95 | |
| | | | 4 | 11 | | | | 70 | |
| | | | 3 | 3 | | | | 110 | |
| | | | 8 | 11 | | | | 16 | * |
| | | | 9 | 9 | | | | 22 | * |
| $\begin{array}{l}CH_2-S-CO-C_3H_7\\|\\CH-O-CO-C_3H_7\\|\\CH_2-S-CO-C_3H_7\end{array}$ | | | | | | | | 35 | * |

[Note]: * These compounds are not included in the general formulae (I), (II), (III) and (IV).

As is made clear from the above results, the S-acyl compounds of the formula (I), (II), (III) or (IV) show a high activity for lipase, and among them BALB shows an extremely high activity. On the contrary, among the compounds which are not included in the formula (I), (II), (III) or (IV), for instance 2-butyroyloxy-1,3-bis-butyroylthiopropane, a positional isomer of BALB, shows less than 1/10 of the relative activity of BALB.

EXAMPLE 13

Preparation of kit for lipase assay (50 assays)

i. Buffer: Tris (i.e. 2-amino-2-hydroxymethyl-1,3-propanediol) (967 parts by weight) and Iris-HCl (380 parts by weight) are triturated well and each 1.6 g of the mixture is weighed into white bottles. When it is used, the mixture is dissolved in water to make a final volume of 120 ml (pH 8.4 – 8.6).

ii. DTNB: DTNB (54 parts by weight) and mannitol (486 parts by weight) are triturated well and each 110 mg of the mixture is weighed into 5 ml-brown bottles. When it is used, the mixture is dissolved in the buffer (i) to make a final volume of 11 ml.

iii. 20 mM PMSF: 0.348 % PMSF in ethanol solution is prepared and each 1.1 ml of the solution is poured into 2.5 ml-brown bottles.

iv. 20 mM BALB: 0.669 % BALB in ethanol solution is prepared and each 11 ml of the solution is poured into 25 ml-brown bottles.

These reagents are kept in the form of a kit. Each kit can be used for 50 determination of lipase activity in the samples according to the procedure described in Example 2.

EXAMPLE 14

Preparation of MPB:

$$\begin{array}{l}CH_2-S-CO-C_3H_7\ (n)\\|\\CH-O-CO-C_3H_7\ (n)\\|\\CH_2-O-CO-C_3H_7\ (n)\end{array}$$

α-Monothioglycerol (3.8 g) is dissolved in pyridine (50 ml) and thereto is added dropwise n-butyric anhydride (17.4 g) at room temperature with stirring. The mixture is heated with stirring on a boiling water bath for 3 hours and then concentrated under reduced pressure. The resulting residue is dissolved in benzene and the solution is washed with dilute hydrochloric acid, water and dilute aqueous potassium carbonate in order, dried over anhydrous magnesium sulfate, and benzene is removed. The residue is distilled under reduced pressure to give the titled compound (9.4 g), colorless liquid, b.p. 162° – 167° C/1 mmHg.

EXAMPLE 15

In the same manner as described in Example 14, various compounds are prepared, which are shown in Table 5.

Table 5

| Compound | Melting or boiling point |
|---|---|
| 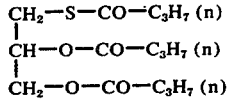 $SCOC_3H_7$ (n) ... $SCOC_3H_7$ (n) | b.p. 185 – 186° C/3 mmHg |
| $SCOC_7H_{15}$ (n) ... $(CH_2)_6$ ... $SCOC_7H_{15}$ (n) | m.p. 40.5 – 41.0° C |
| $\begin{array}{l}(CH_2)_2SCOC_3H_7\ (n)\\|\\O\\|\\(CH_2)_2SCOC_3H_7\ (n)\end{array}$ | b.p. 157 – 160° C/2 mmHg |
| $\begin{array}{l}(CH_2)_2SCOC_3H_7\ (n)\\|\\S\\|\\(CH_2)_2SCOC_3H_7\ (n)\end{array}$ | b.p. 170 – 173° C/2 mmHg |
| $\begin{array}{l}CH_2SCOC_3H_7\ (n)\\|\\CHSCOC_3H_7\ (n)\\|\\CH_2OCOC_3H_7\ (n)\end{array}$ | b.p. 143 – 146° C/0.15 mmHg |
| $\begin{array}{l}CH_2SCOC_3H_7\ (n)\\|\\CH_2OCOC_3H_7\ (n)\end{array}$ | b.p. 112 – 114° C/3 mmHg |

EXAMPLE 16

Preparation of the compound:

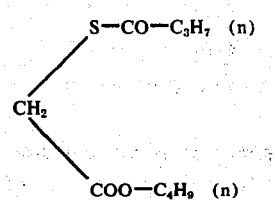

α-n-Butyroylmercaptoacetic acid (6 g) and p-toluene-sulfonic chloride (7 g) are dissolved in benzene (50 ml) and thereto are added triethylamine (9.4 g) and then n-butylalcohol (2.8 g) at room temperature with stirring. The mixture is heated on a water bath at 50° C for 30 minutes. After cooling, the mixture is washed with cold water and aqueous sodium hydrogen carbonate in order, dried over anhydrous magnesium sulfate, and benzene is removed. The residue is distilled under reduced pressure to give the desired compound (6.5 g), colorless liquid, b.p. 122° – 124° C/4 mmHg.

EXAMPLE 17

In the same manner as described in Example 16, various compounds are prepared, which are shown in Table 6.

Table 6

| Compound | Boiling point |
| --- | --- |
| 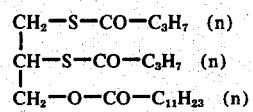 | b.p. 143 – 145° C/1 mmHg |
| 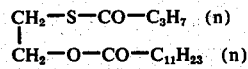 | b.p. 135 – 140° C/0.3 mmHg |

EXAMPLE 18

Preparation of the compound:

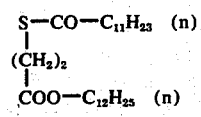

β-Lauroylmercaptopropionic acid (4.0 g) and p-toluenesulfonyl chloride (2.64 g) are dissolved in benzene (50 ml) and thereto are added triethylamine (3.51 g) and then n-dodecylalcohol (2.58 g). The mixture is treated in the same manner as described in Example 16. The resulting residue is recrystallized from ethanol to give the titled compound (5 g), m.p. 36° – 37° C.

EXAMPLE 19

Preparation of the compound:

$$CH_2-S-CO-C_3H_7 \ (n)$$
$$CH-S-CO-C_3H_7 \ (n)$$
$$CH_2-O-CO-C_{11}H_{23} \ (n)$$

2,3-Dimercaptopropanol (12.0 g) is dissolved in benzene (75 ml) and thereto is added dropwise lauroyl chloride (21.5 g) with stirring. The mixture is refluxed with stirring for about 3.5 hours until the generation of hydrogen chloride is ceased to evolve. The mixture is then distilled to remove benzene and the resulting residue is distilled to give 2,3-dimercaptopropyl laurate (11.5 g) as a yellow oily substance, b.p. 167° – 175° C/1 mmHg.

I.R. spectrum (film): 2563, 1738 (cm$^{-1}$).

2,3-Dimercaptopropyl laurate (10 g) and pyridine (11.8 g) are dissolved in benzene (50 ml) and thereto is added dropwise n-butyric anhydride (10.3 g) at room temperature with stirring. The mixture is refluxed with stirring for 4 hours. The reaction mixture is shaken with an aqueous potassium carbonate, washed with water, dried and distilled to remove benzene. The residue is chromatographed on a silica gel column, which is washed with n-hexane and then eluted with benzene to obtain the titled compound (8.0 g) as the yellow oily substance.

I.R. spectrum (film): 1742, 1698 (cm$^{-1}$).

EXAMPLE 20

Preparation of the compound:

$$CH_2-S-CO-C_3H_7 \ (n)$$
$$CH_2-O-CO-C_{11}H_{23} \ (n)$$

Thiolauric acid (15 g) is dissolved in dry ethanol (50 ml) and thereto is added a solution of ethylene oxide (15 ml) in cold dry ethanol (20 ml) and the mixture is allowed to stand at room temperature overnight. The solvent is distilled off under reduced pressure and the resulting residue is recrystallized from petroleum ether to give colorless scales of S-lauroylmercaptoethanol (8 g), m.p. 45° – 46° C (SH test with DTNB: negative).

S-Lauroylmercaptoethanol (5 g) is heated in an oil bath at 190° C for 3 hours to give O-lauroylmercaptoethanol, b.p. 153° – 155° C/3 mmHg (SH indication: positive).

O-Lauroylmercaptoethanol (1 g) thus obtained is mixed with n-butyric anhydride (4.5 ml) and the mixture is heated in an oil bath at 190° – 200° C for 2 hours, and then concentrated under reduced pressure to remove n-butyric acid and excess n-butyric anhydride. The resulting residue is cooled and the precipitated crystals are recrystallized from ethanol twice to give S-butyroyl-O-lauroylmercaptoethanol (1 g), m.p. about 25° C, b.p. 190° – 195° C/3 mmHg.

What is claimed is:

1. A reagent for determining lipase activity comprising a chromogenic sulfhydryl reagent and, as an active ingredient one of the S-acyl compounds of the formula:

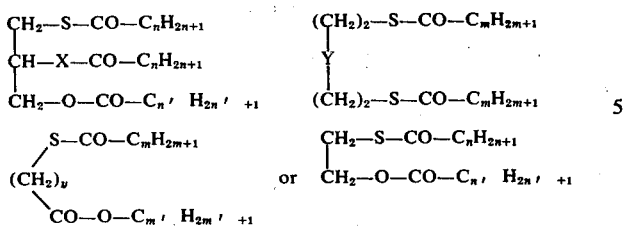

wherein $n$ is an integer of 2 to 4, inclusive; $n'$ is an integer of 2 to 4, inclusive or of 9 to 13, inclusive; $m$ is an integer of 3, 7 or 11; $m'$ is an integer of 4 or 12, $y$ is an integer of 1 or 2; X is sulfur atom or oxygen atom; Y is sulfur atom, oxygen atom or ethylene group; provided that when $y$ is 1, $m'$ oxygen atom or ethylene group; provided that when $y$ is 1, $m'$ is 4 and when $y$ is 2, $m'$ is 12.

2. The reagent according to claim 1, wherein the S-acyl compound is the one of the formula:

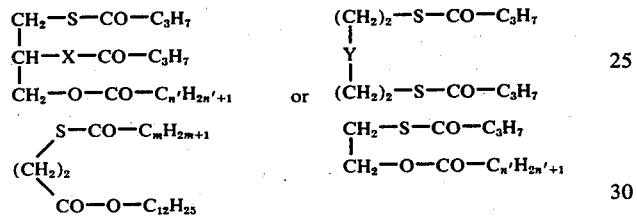

wherein $n'$ is an integer of 3 or 11; $m$ is an integer of 3, 7 or 11; X is sulfur atom or oxygen atom; and Y is sulfur atom, oxygen atom or ethylene group.

3. The reagent according to claim 1, wherein the S-acyl compound is the one of the formula:

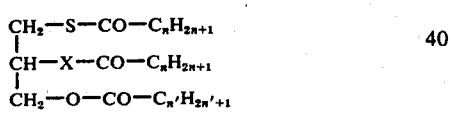

wherein $n$ is an integer of 2 to 4, inclusive; $n'$ is an integer of 2 to 4, inclusive or of 9 to 13, inclusive; and X is sulfur atom or oxygen atom.

4. The reagent according to claim 1, wherein the S-acyl compound is the one of the formula:

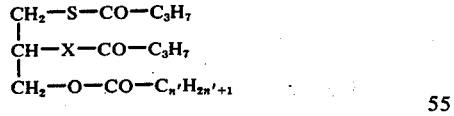

wherein $n'$ is an integer of 2 to 4, inclusive or of 9 to 13, inclusive; and X is sulfur atom or oxygen atom.

5. The reagent according to claim 1, wherein the S-acyl compound is the one of the formula:

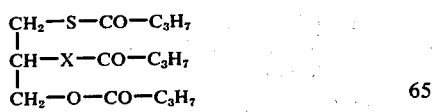

wherein X is sulfur atom or oxygen atom.

6. The reagent according to claim 1, wherein the S-acyl compound is the one of the formula:

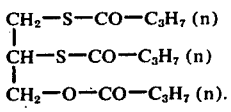

7. The reagent according to claim 1, wherein the S-acyl compound is the one of the formula:

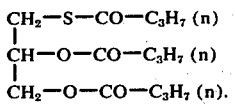

8. The reagent according to claim 1, wherein the S-acyl compound is the one of the formula:

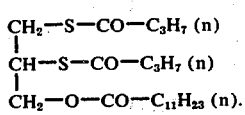

9. The reagent according to claim 1, wherein the S-acyl compound is the one of the formula:

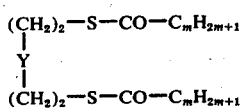

wherein $m$ is an integer of 3, 7 or 11; and Y is sulfur atom, oxygen atom or ethylene group.

10. The reagent according to claim 1, wherein the S-acyl compound is the one of the formula:

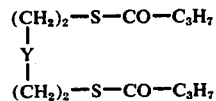

wherein Y is sulfur atom, oxygen atom or ethylene group.

11. The reagent according to claim 1, wherein the S-acyl compound is the one of the formula:

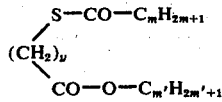

wherein $m$ is an integer of 3, 7 or 11; $m'$ is an integer of 4 or 12; and $y$ is an integer of 1 or 2; provided that when $y$ is 1, $m'$ is 4 and when $y$ is 2, $m'$ is 12.

12. The reagent according to claim 1, wherein the S-acyl compound is the one of the formula:

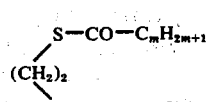

wherein $m$ is an integer of 3, 7 or 11.

13. The reagent according to claim 1, wherein the S-acyl compound is the one of the formula:

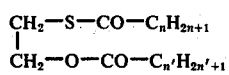

wherein $n$ is an integer of 2 to 4, inclusive; and $n'$ is an integer of 2 to 4, inclusive or of 9 to 13, inclusive.

14. The reagent according to claim 1, wherein the S-acyl compound is the one of the formula:

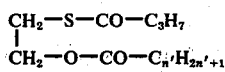

wherein $n'$ is an integer of 2 to 4, inclusive or of 9 to 13, inclusive.

15. The reagent according to claim 1, wherein the S-acyl compound is the one of the formula:

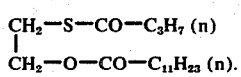

16. A method for determining lipase activity, which comprises subjecting one of the S-acyl compounds of the formula:

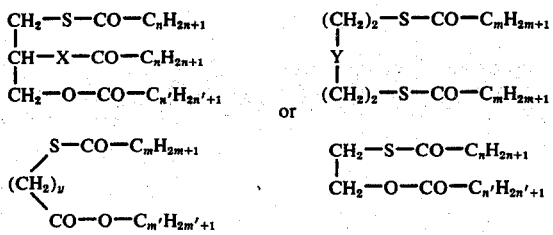

wherein $n$ is an integer of 2 to 2, inclusive; $n'$ is an integer of 2 to 4, inclusive or of 9 to 13, inclusive; $m$ is an integer of 3, 7 or 11; $m'$ is an integer of 4 or 12; $y$ is an integer of 1 or 2; X is sulfur atom or oxygen atom; Y is sulfur atom, oxygen atom or ethylene group; provided that when $y$ is 1, $m'$ is 4 and when $y$ is 2, $m'$ is 12, to the lipolytic action of lipase in a buffer solution containing a chromogenic sulfhydryl reagent and then subjecting the resulting SH-compound obtained by the hydrolysis of the above S-acyl compound to a colorimetry with the chromogenic sulfhydryl reagent.

17. The method according to claim 16, wherein the buffer is Tris-HCl buffer.

18. The method according to claim 16, wherein a carboxylesterase and/or arylesterase inhibitor is added to the reaction system prior to the reaction of S-acyl compound and lipase.

19. The method according to claim 18, wherein the enzyme inhibitor is a member selected from the group consisting of phenylmethylsulfonyl fluoride and diisopropylfluorophosphate.

20. The method according to claim 18, wherein the enzyme inhibitor is phenylmethylsulfonyl fluoride.

21. The method according to claim 20, wherein the phenylmethylsulfonyl fluoride is used in a concentration of 0.03 to 3 mM.

22. The method according to claim 20, wherein the phenylmethylsulfonyl fluoride is used in a concentration of 0.1 to 1.5 mM.

23. The method according to claim 20, wherein the phenylmethylsulfonyl fluoride is used in a concentration of 0.2 to 0.8 mM.

24. The method according to claim 20, wherein the phenylmethylsulfonyl fluoride is used in a concentration of 0.3 to 0.5 mM.

25. The method according to claim 16, wherein acetone is added to the reaction mixture of the S-acyl compound and lipase to stop the reaction.

26. The method according to claim 16, wherein the chromogenic sulfhydryl reagent is 5,5'-dithiobis(2-nitrobenzoic acid).

27. The method according to claim 18, wherein the buffer is Tris-HCl buffer, the enzyme inhibitor is phenylmethylsulfonyl fluoride in the range of 0.3 to 0.5 mM and the chromogenic sulfhydryl reagent is 5,5'-dithiobis(2-nitrobenzoic acid).

28. The method according to claim 18, which is applied to the determination of lipase activity in human serum.

29. The method according to claim 16, wherein the S-acyl compound is the one of the formula:

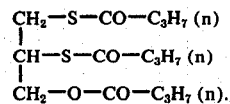

30. The method according to claim 16, wherein the S-acyl compound is the one of the formula:

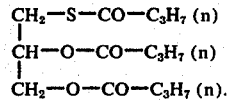

31. A kit for the determination of lipase activity comprising
a. one of the S-acyl compounds of the formula:

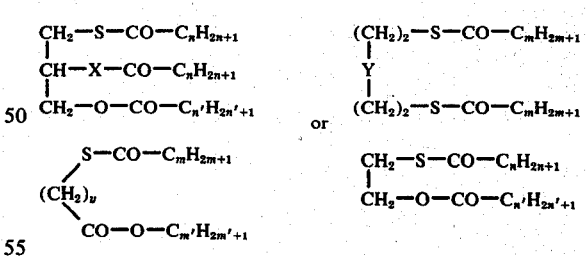

wherein $n$ is an integer of 2 to 4, inclusive; $n'$ is an integer of 2 to 4, inclusive or of 9 to 13, inclusive; $m$ is an integer of 3, 7 or 11; $m'$ is an integer of 4 or 12; $y$ is an integer of 1 or 2; X is sulfur atom or oxygen atom; Y is sulfur atom, oxygen atom or ethylene group; provided that when $y$ is 1, $m'$ is 4 and when $y$ is 2, $m'$ is 12,
b. a buffer,
c. a chromogenic sulfhydryl reagent, and
d. a carboxylesterase and/or arylesterase inhibitor 32. The kit according to claim 31, wherein the S-acyl compound is in the form of a solution in an alcohol.

33. The kit according to claim 31, wherein the buffer (b) is Tris-HCl buffer.

34. The kit according to claim 31, wherein the buffer (b) is in the form of a powder.

35. The kit according to claim 31, wherein the chromogenic sulfhydryl reagent (c) is 5,5′-dithiobis(2-nitrobenzoic acid).

36. The kit according to claim 31, wherein the chromogenic sulfhydryl reagent (c) is a mixed powder of 5,5′-dithiobis (2-nitrobenzoic acid) and an inert powder.

37. The kit according to claim 36, wherein the inert powder is mannitol.

38. The kit according to claim 31, wherein the enzyme inhibitor (d) is phenylmethylsulfonyl fluoride.

39. The kit according to claim 31, wherein the S-acyl compound is the one of the formula:

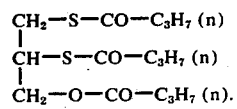

40. The kit according to claim 31, wherein the S-acyl compound is the one of the formula:

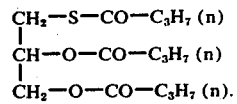

41. The reagent according to claim 1 wherein the chromogenic sulfhydryl reagent is 5,5′-dithiobis(2-nitrobenzoic acid).

* * * * *